United States Patent
Muramatsu et al.

(10) Patent No.: US 7,413,545 B2
(45) Date of Patent: Aug. 19, 2008

(54) METHOD OF CALCULATING CIRCULATION DYNAMICS OF A LIVING BODY

(75) Inventors: Hiroyuki Muramatsu, Chiba (JP); Minao Yamamoto, Chiba (JP); Takashi Nakamura, Chiba (JP); Takahiko Nakamura, Chiba (JP); Masataka Shinogi, Chiba (JP)

(73) Assignee: Seiko Instruments Inc. (JP)

( * ) Notice: Subject to any disclaimer, the term of this patent is extended or adjusted under 35 U.S.C. 154(b) by 646 days.

(21) Appl. No.: 10/405,128

(22) Filed: Apr. 2, 2003

(65) Prior Publication Data

US 2003/0191399 A1    Oct. 9, 2003

(30) Foreign Application Priority Data

Apr. 3, 2002    (JP)    ............................. 2002-101230

(51) Int. Cl.
*A61B 5/02*    (2006.01)
*A61B 5/00*    (2006.01)
(52) U.S. Cl. ................. 600/481; 600/485; 600/504; 600/301
(58) Field of Classification Search ........................ None
See application file for complete search history.

(56) References Cited

U.S. PATENT DOCUMENTS

| 4,562,843 | A | * | 1/1986 | Djordjevich et al. | ......... 600/485 |
| 6,113,543 | A | * | 9/2000 | Bonnefous | ................. 600/438 |
| 6,767,329 | B2 | * | 7/2004 | Amano et al. | ............... 600/500 |

OTHER PUBLICATIONS

"Information on the Results of Food Research", Issue 11, Jun. 1999, Food Experiment Research Promotion Council, National Food Research Institute, Tsukuba, Japan.
Kikuchi, Y. et al., "Distribution, average and normal range of whole blood passage time in healthy students:Comparison of institute workers and university students," Hemorheology and Related Research, vol. 1, 1998, pp. 53-57.
Patent Abstracts of Japan, publication No. 01-214335, publication date Aug. 8, 1989.

* cited by examiner

*Primary Examiner*—Charles A. Marmor, II
*Assistant Examiner*—Patricia Mallari
(74) *Attorney, Agent, or Firm*—Adams & Wilks

(57) ABSTRACT

In a method of calculating circulation dynamics of a living body, a resistance component corresponding to a shape of a blood vessel in the living body is derived using previously obtained values of viscosity, pressure and flow rate of blood flowing in the blood vessel. Information corresponding to the viscosity of the blood is calculated using the derived resistance component.

6 Claims, 16 Drawing Sheets

METHOD OF CALCULATING CIRCULATION DYNAMICS OF A LIVING BODY

BACKGROUND OF THE INVENTION

1. Field of the Invention

The present invention is directed to sensor technology and relates in general to an apparatus for measuring a body fluid circulating a living body and a tissue constituting a circulatory organ.

In particular, the invention relates to a technology for grasping a state of blood in distal end part to carry out an evaluation of health, a diagnosis of a disease, an evaluation of medicines, and the like.

2. Description of the Related Art

Heretofore, for the purpose of carrying out the evaluation of health of a living body, the diagnosis of a disease, the determination of an influence of medicines exerted on a living body, and the like, there have been proposed various methods utilizing information obtained from blood. In terms of a medical treatment for example, there is a method in which the blood is collected from a living body, and the blood concerned is applied to a component analyzer to obtain a circulation information from a rate of the various blood components contained in the blood to thereby evaluate the health state of the living body, and the like.

Here, circulation dynamics means a state in which the blood and a lymph fluid which are moved through the inside of the circulatory organ to supply tissues and cells of a living body with oxygen and nutrition to carry carbon dioxide gas and wastes away vary continuously with time. For example, a blood flow rate, a change in blood flow, a flow property, a pulse wave and the like correspond to the circulation dynamics.

However, this method is not suitable for the case where the circulation dynamics needs to be measured to evaluate the health state of a living body at locations away from medical facilities, and the case where the circulation dynamics needs to be measured to evaluate regularly the health state of the living body with the circulation dynamics measuring apparatus being usually mounted to a living body because when the blood is collected, a living body needs to be pricked with an injection needle. Then, there has been developed an apparatus with which a wave is noninvasively inputted from a surface of a living body into the living body to be reflected by the body fluid flowing through the living body, in particular, the blood, and then, the blood state is analyzed on the basis of the motion and the position to measure the circulation dynamics to thereby evaluate the health state.

On the other hand, as for a prior art of evaluating medically the health evaluation, there is known the method made by Yuji Kikuchi and entitled "Measurement of total blood flowability using a capillary model," Food Research Result Information (medical journal), No. 11, 1999, i.e., a method in which the blood is collected from a subject and a blood rheology is measured on the basis of a passing time of the blood flow under the constant pressure using a micro-channel array made by a lithographic technique. This method is used, whereby the blood rheology can be measured as the circulation information, and also, the health state can be evaluated on the basis of the resultant value.

In addition, as for a prior art of evaluating noninvasively the health in a home or the like, there is known a method in which a wave such as light is transmitted from a skin surface of a living body to the living body to receive the reflected light to thereby detect the flow rate of the blood flowing through a blood vessel. That is, this method is such that the detected flow rate is differentiated to obtain an acceleration pulse wave as one of the circulation information to thereby evaluate the health state. Here, FIG. 15 is a block diagram showing an internal configuration of a signal processing portion 600 of a conventional circulation information measuring apparatus., and a state of connection between the signal processing portion 600 and a circulation sensor portion 607.

As shown in the figure, the signal processing portion 600 is schematically constituted by a driving portion (light emitting portion) 601, a reception portion (light receiving portion) 602, a signal arithmetic operation portion 603, and an output portion 604. The driving portion (light emitting portion) 601 lights a light emitting element 605 installed in a circulation sensor 607 to transmit a driving energy adapted to apply the light towards a blood vessel. The reception portion (light receiving portion) 602 amplifies a signal which is generated at the time when a photoelectric receiving element 606 installed in the circulation sensor 607 subjects the light applied thereto to the photoelectric conversion. The signal arithmetic operation portion 603 executes a processing program stored in a memory region (not shown) provided therein to execute various processings concerned with the measurement of the circulation information to thereby output the processing results to the output portion 604. Then, the signal arithmetic operation portion 603 converts a level of the received signal into a quantity of change in blood volume, and then, differentiates the resultant value twice to thereby obtain the acceleration pulse wave as the circulation information.

In addition, FIG. 16 is a block diagram showing a configuration of an example of a conventional system for measuring quantitatively the blood flow rate. This system is constituted by a flow rate measuring system 702 and a blood vessel diameter measuring system 701. An ultrasonic wave probe 706 is placed perpendicularly to a blood vessel 705, whereby an ultrasonic wave beam is applied to the blood vessel 705 and a diameter of the blood vessel is measured on the basis of an echo from the wall of the blood vessel, and the blood flow velocity is measured with two other ultrasonic wave probes 707 and 708. The two ultrasonic wave beams are used, whereby the flow rate of the blood can be measured on the basis of the angle between the two ultrasonic wave beams irrespective of the angle between the ultrasonic wave beam and the blood vessel, and the diameter of the blood vessel and the blood velocity which have been measured are processed by a microcomputer 703, and the resultant data is displayed as the blood flow rate on a display device 704.

However, in the blood rheology measuring apparatus using the micro-channel array, since the blood is collected from a subject by any means, his/her elbow portion must be pricked with an injection needle using a syringe to collect the blood. Thus, a subject needs to go to a medical facility or the like for the collection of blood. In addition, in the case where as shown in the prior art, a wave is inputted through a skin surface of a living body into the living body to be reflected by the body fluid flowing through the living body to analyze the blood state from the motion and the position of the reflected wave to thereby obtain the circulation information in order to evaluate the health state of a subject, contraction (strain) and slackness of a blood vessel in a living body (change in diameter of a blood vessel) exerts an influence on a fluid state of the blood in the living body to change the circulation information. Hence, it becomes difficult to measure the circulation information with which an essential health state should be evaluated. In addition, since the fluid state of the blood is also changed due to fluctuation in a blood pressure, when evaluating the circulation dynamics, it is necessary to take a change in blood vessel and blood pressure into consideration.

Moreover, in the conventional blood flow measuring system, it is necessary to use an ultrasonic wave prove for measurement of a diameter of a blood vessel and ultrasonic wave probes for measurement of a blood flow. If independent probes are used, since alignment thereof is difficult to be carried out, it is difficult to measure a diameter of a blood vessel and a blood flow velocity in the same position within a blood vessel, and also, there is a limit to the miniaturization. Further, since the independent probes are used, there is a problem in that since dispersion in sensitivity is difficult to be adjusted for the probes, such probes are unsuitable for mass production, and so forth.

Since in the measurement of the circulation dynamics of a distal end part (e.g., the tip of a finger) of a living body, a measurement area is narrow and a diameter of a blood vessel is also small, in the system as in the prior art in which there is a limit to the miniaturization, there is also a problem in that it is difficult to measure the circulation dynamics of a distal end part of a living body.

Furthermore, since no influence of the blood pressure is taken into consideration, the accurate evaluation is impossible from a viewpoint of the evaluation of the circulation dynamics.

In the light of the foregoing, the present invention has been made in order to solve the above-mentioned problems associated with the prior art, and therefore, the present invention aims at measuring the circulation information with high accuracy irrespective of the degree of strain of a blood vessel of a part to be measured in a living body when a wave is noninvasively inputted through a skin surface of the living body to be reflected by the body fluid flowing through the living body, and then, the state of the blood and the like is analyzed on the basis of the motion and the position of the reflected wave to obtain the circulation information in order to evaluate the health state.

In addition, it is an object of the present invention to provide a circulation dynamics sensor which is capable of measuring the circulation dynamics with accuracy even in a part to be measured having a narrow measurement area and a small blood vessel diameter.

SUMMARY OF THE INVENTION

In view of the above, according to the present invention, there are provided a circulation dynamics measuring apparatus; a circulation dynamics measuring method; a blood pressure measuring method; and a circulation dynamics sensor. The circulation dynamics measuring apparatus includes: a circulation sensor portion for transmitting and receiving a wave to and from the inside of a living body through a surface of the living body; and a processing portion for calculating a circulation dynamics on the basis of the received wave, in which the circulation sensor portion has means for measuring a blood flow rate and means for measuring a blood pressure, and the processing portion calculates an information concerned with viscosity of the blood on the basis of the measured blood pressure and blood flow rate.

Further, according to the present invention, there is provided a circulation dynamics measuring apparatus including: a circulation sensor portion for transmitting and receiving a wave to and from the inside of a living body through a surface of the living body; and a processing portion for calculating a circulation dynamics on the basis of the received wave, in which the circulation sensor portion has means for measuring a blood flow rate and means for measuring a blood pressure, and the processing portion derives a resistance component concerned with a shape of the blood vessel on the basis of a viscosity value of the blood which is measured by collecting the blood in advance, and the measured blood pressure and blood flow rate.

Further, the method of the present invention includes: deriving a resistance component concerned with a shape of a blood vessel on the basis of a viscosity value, a blood pressure and a blood flow rate of blood which are measured in advance; and calculating information concerned with the viscosity of the blood on the basis of the blood pressure and the blood flow rate.

Further, the method of the present invention includes: measuring a blood flow rate; calculating a resistance of a blood vessel of a subject on the basis of the blood flow rate, and a blood pressure value which is measured in advance; and calculating a blood pressure value of the subject on the basis of the blood vessel resistance and the blood flow rate.

Further, according to the present invention, there is provided a circulation dynamics sensor having at least two sheets of piezoelectric devices for transmitting and receiving an ultrasonic wave, at least one sheet of the piezoelectric devices serving to measure a blood flow velocity, at least the other sheet of the piezoelectric devices serving to measure a blood vessel diameter, in which the piezoelectric device for measuring a blood flow velocity, and the piezoelectric device for measuring a blood vessel diameter are arranged on the same substrate.

Further, the present invention has a structure in which the piezoelectric devices for measuring a blood vessel diameter are provided by plural sheets.

Further, according to the present invention, there is provided a structure in which a driving frequency of the piezoelectric device for measuring a blood vessel diameter is different from that of the piezoelectric device for measuring a blood flow velocity.

Further, according to the present invention, there is provided a structure in which each of the piezoelectric devices has a rectangular shape, and the piezoelectric device for measuring a blood flow velocity and the piezoelectric device for measuring a blood vessel diameter are arranged so that their longitudinal extension lines intersect perpendicularly with each other.

Further, according to the present invention, there is provided a structure in which a piezoelectric device is arranged on a back surface with respect to the surface of the substrate on which the piezoelectric devices are arranged.

Further, according to the present invention, there is provided a circulation dynamics measuring apparatus having the circulation dynamics sensor, a driving circuit for driving the piezoelectric devices, and a processing portion for processing a wave received by the piezoelectric device, in which the piezoelectric device for measuring a blood vessel diameter and the piezoelectric device for measuring a blood flow velocity are driven with their operation timings being shifted from each other.

BRIEF DESCRIPTION OF THE DRAWINGS

The above and other objects as well as advantages of the present invention will become clear by the following description of the preferred embodiments of the present invention with reference to the accompanying drawings, wherein.

DETAILED DESCRIPTION OF THE PREFERRED EMBODIMENTS

Figure 1:
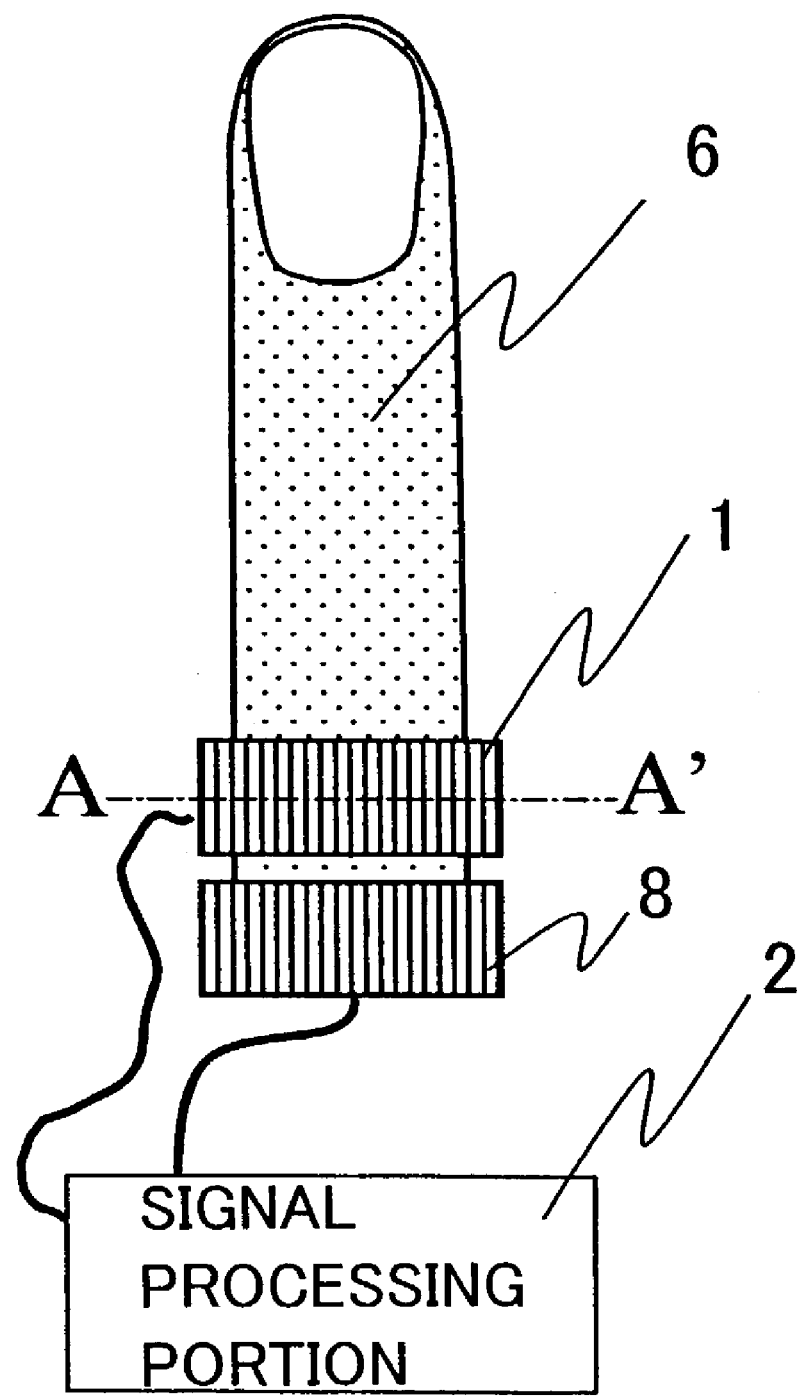
FIG. 1 is a schematic view, partly in block diagram, useful in explaining construction of a finger ring portion, a signal processing portion and a blood pressure measuring portion according to a first embodiment of the present invention.

Preferred embodiments of the present invention will hereinafter be described in detail with reference to the accompanying drawings.

Measurement principles of a circulation dynamics measuring apparatus of the present invention is such that circulation information is obtained from a time change of circulation components appearing when pulses pulsate, e.g., a blood flow velocity, a blood pressure and a diameter of a blood vessel. Then, the circulation dynamics measuring apparatus of the present invention has a circulation sensor portion for transmitting a wave from a surface of a living body to the inside of the living body, and for receiving a reflected wave from the inside of the living body to the surface of the living body, and a processing portion for calculating the circulation dynamics from the received wave. In the circulation dynamics measuring apparatus, the circulation sensor portion has such a configuration as a basic configuration as to have a portion for measuring a blood pressure and a blood flow rate, and the health state of the living body is evaluated from such circulation information.

As for indexes of the circulation dynamics of a distal end part of a living body, there are given a blood flow velocity and a blood flow rate of a blood vessel of the distal end part. However, if it is taken into consideration that as described above, a diameter of a blood vessel is changed due to a strain state and a temperature, and a blood flow rate is also changed due to a value of a blood pressure, only these indexes are insufficient as the measurement information. If a blood vessel in the distal end part is substituted for an electric circuit, then a blood flow rate Q corresponds to a current, and a difference in blood pressure between two different points within the blood vessel corresponds to a voltage V. Note that the blood flow rate Q means a quantity of blood passing through a certain point in the blood vessel per unit time. Since both the above-mentioned blood flow velocity and blood flow rate are the results of measurement of part of the blood flow rate Q or the blood flow rate Q itself, it is concluded that they are insufficient as the measurement information.

Here, when a resistance R of a blood vessel is considered as the ratio of V to Q, the following Expression (1) is established:

Blood vessel resistance $R$=blood pressure difference $V$/blood flow rate $Q$  (Expression 1).

R can be considered as the resistance component in the electric circuit.

Note that a shape primary factor such as a thickness of a blood vessel, and a primary factor of viscosity of blood are added to the blood vessel resistance R. When r is the shape primary factor (blood vessel shape resistance component), and p is the primary factor of viscosity of the blood, the following Expression (1') is established:

$R=r\times p$=blood pressure difference $V$/blood flow rate $Q$ (Expression 1).

Since it is difficult to consider that r is largely changed day by day in the same subject, it is considered that R is greatly influenced by the viscosity of the blood. For this reason, for a relatively short period of time (several days), a fluctuation of R can be regarded as a change in viscosity p of the blood.

For this reason, the resistance R of the blood vessel is measured every day, or the resistance R of the blood vessel is measured before and after a specific food is ingested, whereby it is possible to be aware of the change in viscosity p of the blood.

Since the blood pressure V is a driving force of the blood flow, the blood pressure difference between two points in the blood vessel functions as a motive force of the blood flow. On the other hand, the resistance R of the blood vessel becomes a physical primary factor of impeding the blood flow within the blood vessel. The resistance is caused due to movement of the blood having viscosity through the blood vessel having a limited diameter, and a part of the energy is lost in the form of heat.

The resistance R of the blood vessel covers all the influences of the blood vessel diameter, the blood flow rate and the blood pressure, and hence, it is considered as being effective as the index of the circulation dynamics. It is a basic principle of the present invention to utilize R as the index of the circulation dynamics of the distal end part.

In addition, it is considered that r is greatly influenced by the age and the distinction of gender. Thus, r can be made such an index that a mean value of the value R for each age and distinction of gender is preserved in the form of a database, and if the measured value R is larger than the mean value, then the viscosity of the blood is judged to be large, while if the measured value R is smaller than the mean value, then the viscosity of the blood is judged to be small.

Note that it is judged that the blood pressure is measured in advance, and its data is inputted by a subject, or for holding the state in which the blood vessel is extended, a portion to be measured is heated or retained with the temperature thereof, whereby even only the measurement of the blood flow velocity can be utilized as the index of the circulation dynamics.

Incidentally, while an ultrasonic wave is generally used as the wave for use in detection of the flow velocity, any other wave such as a laser beam may also be used.

Circulation information measuring apparatuses according to embodiments of the present invention will hereinbelow be described with reference to the accompanying drawings.

First Embodiment

A first embodiment of the circulation dynamics measuring apparatus of the present invention will now be described with reference to FIGS. 1 to 5. In this embodiment, a basic construction of the circulation dynamics measuring apparatus of the present invention will be described.

Figure 2:
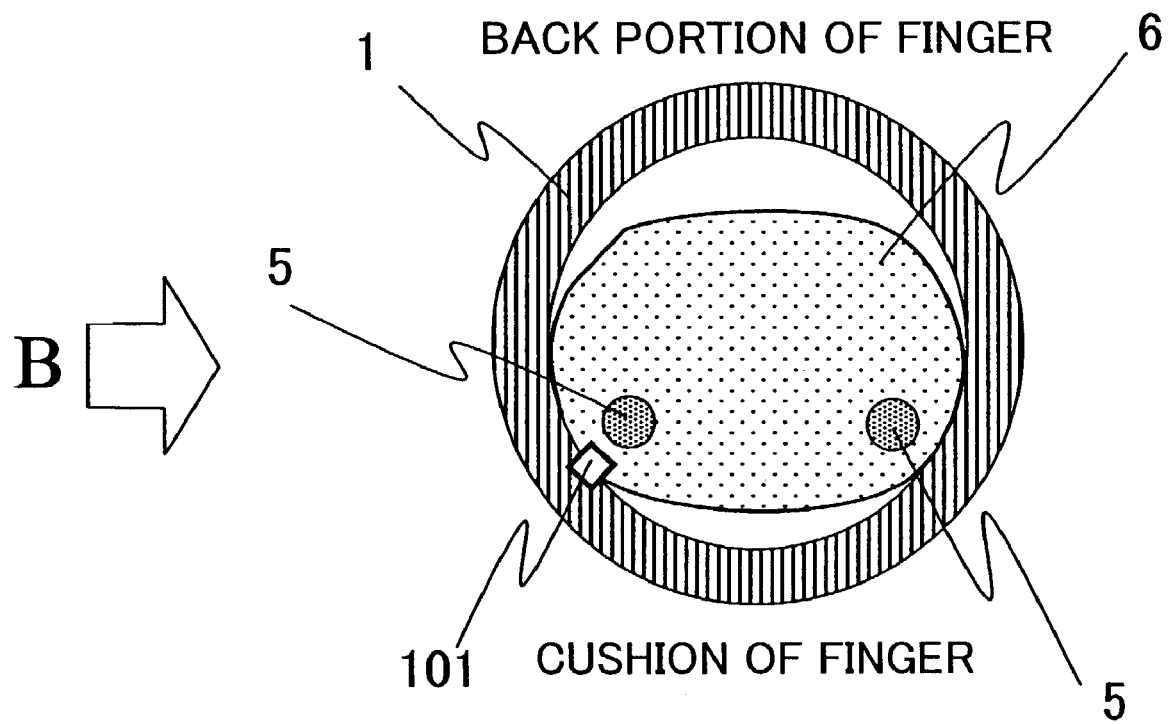
FIG. 2 is a cross sectional view taken along the line A-A' of FIG. 1.
Figure 3:
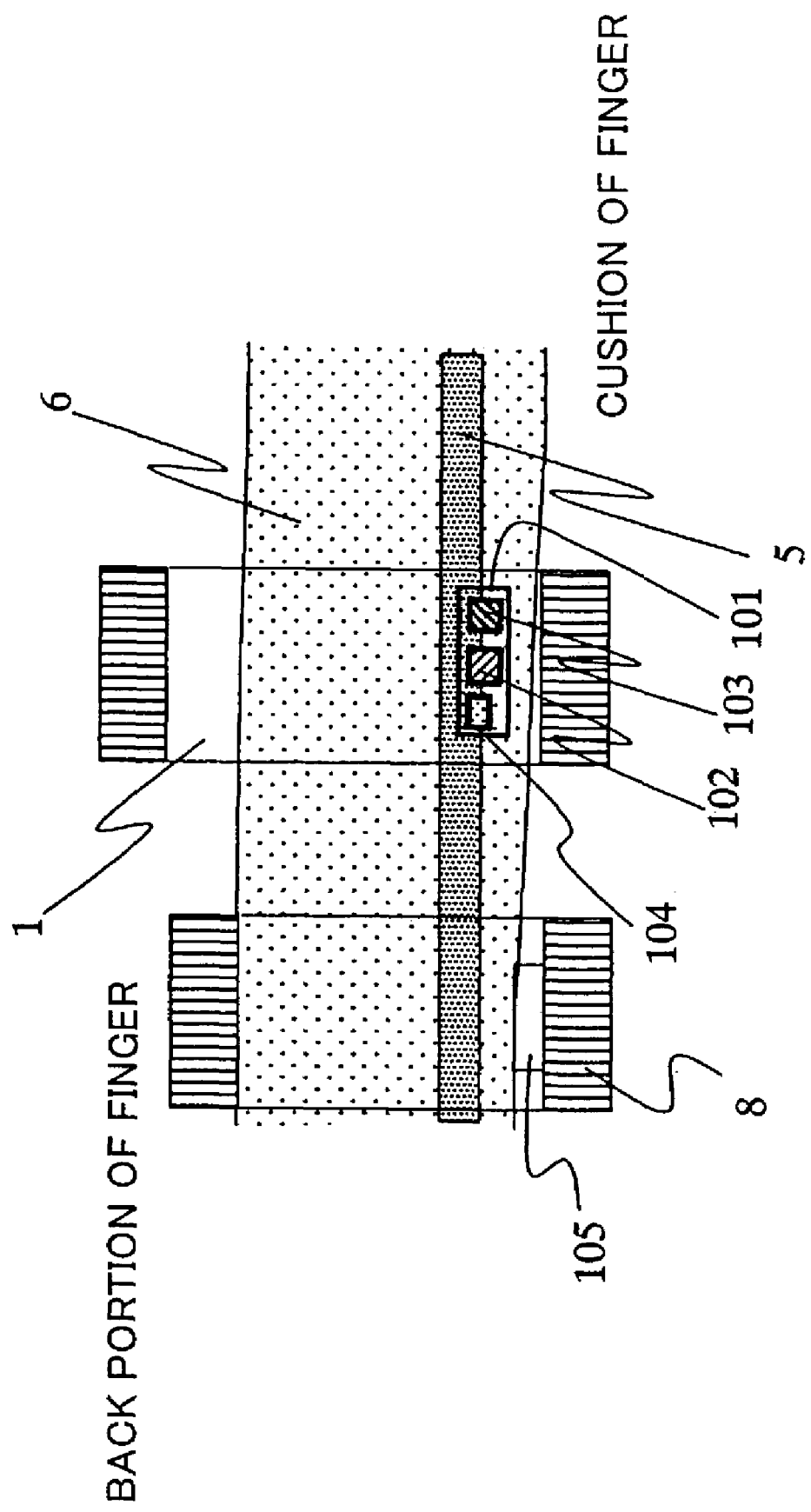
FIG. 3 is a cross sectional view when viewed from a direction indicated by an arrow B in FIG. 2.
Figure 4:
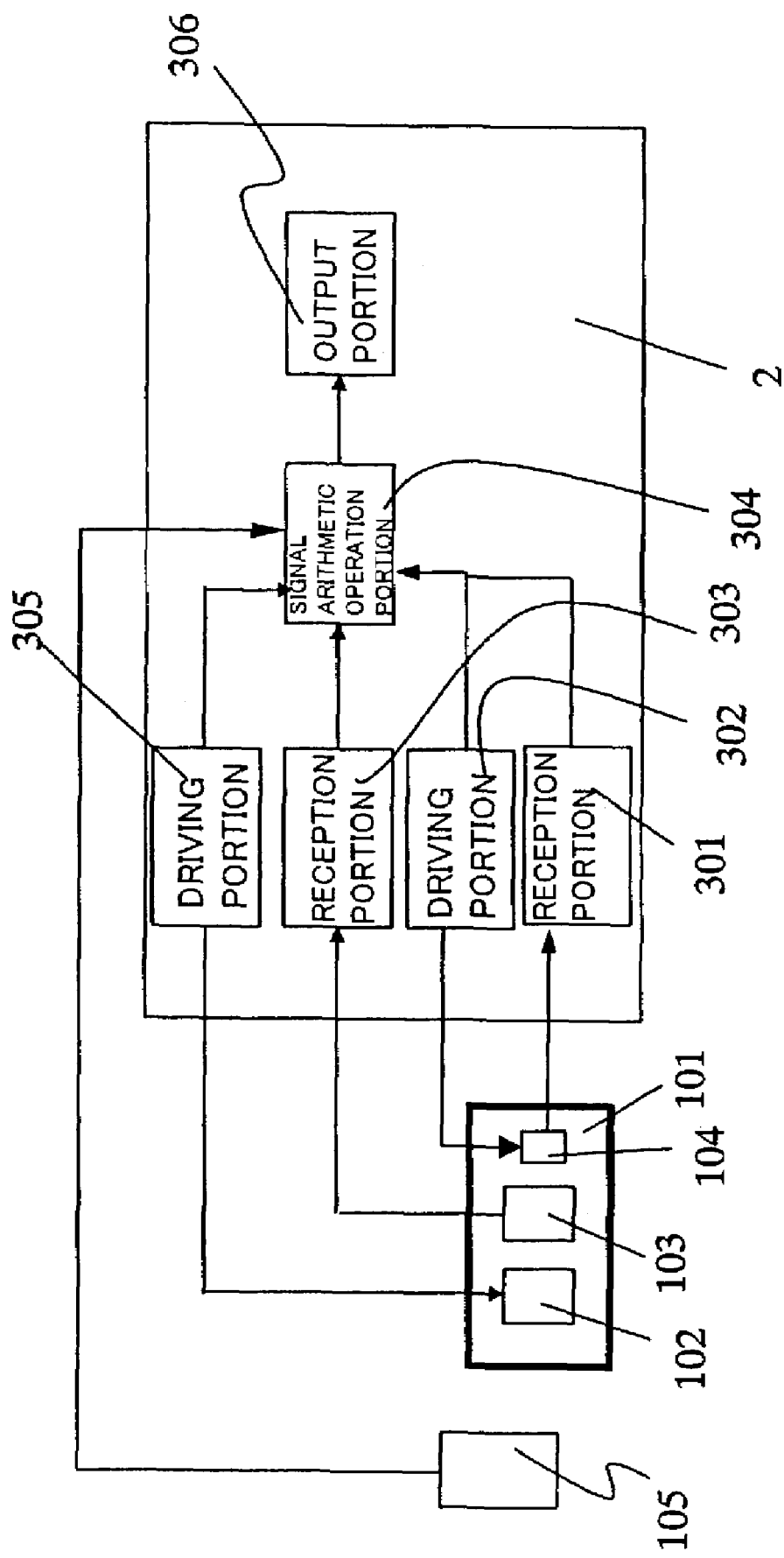
FIG. 4 is a block diagram showing a configuration of the processing portion according to the first embodiment.
Figure 5:
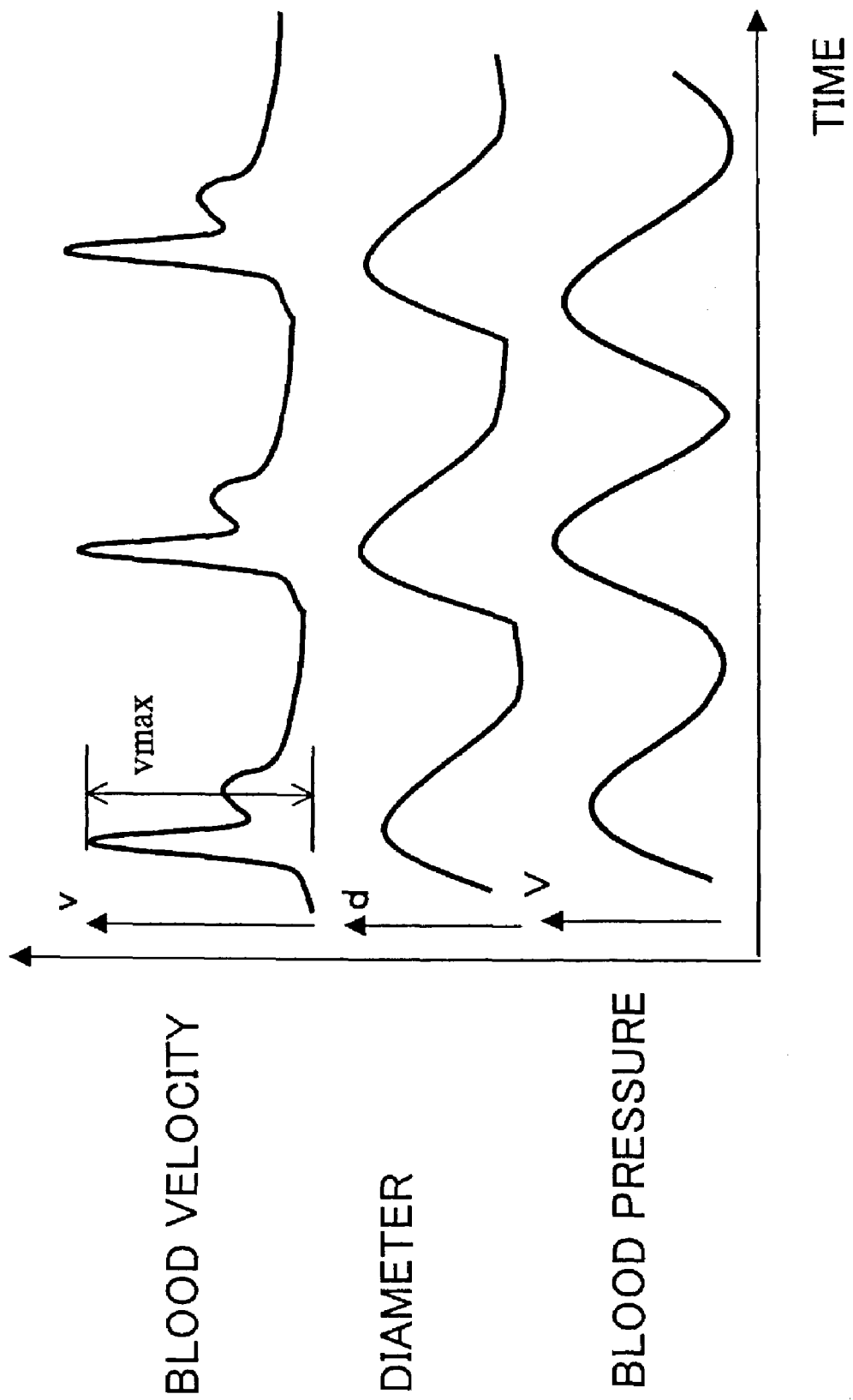
FIG. 5 is a waveform chart useful in explaining the fluctuation in blood flow velocity, blood pressure and blood vessel diameter.

FIG. 1 is a schematic view, partly in block diagram, showing a construction, on an external appearance, of the circulation dynamics measuring apparatus according to this embodiment of the present invention, FIG. 2 is a cross sectional view taken along the line A-A' of FIG. 1, FIG. 3 is a cross sectional view of a finger ring portion 1, FIG. 4 is a block diagram showing a configuration of a signal processing portion, and FIG. 5 is a waveform chart useful in explaining a fluctuation of a measured blood pressure, blood flow velocity and blood vessel diameter. As shown in FIG. 1, the circulation dynamics measuring apparatus is configured so as to be divided into three portions of a finger ring portion 1, a signal processing portion 2 and a blood pressure measuring portion 8.

FIG. 2 shows a cross sectional view taken along the line A-A' of FIG. 1. As shown in FIG. 2, a circulation sensor 101 is present inside the finger ring portion 1. A perspective view of the inside of a ring when viewed from a direction indicated by an arrow B in FIG. 2 is shown in FIG. 3. A piezoelectric device 102 for measuring a blood flow velocity, a piezoelectric device 103 for measuring a blood flow velocity and a piezoelectric device 104 for measuring a blood vessel diameter of the circulation sensor 101 are attached to the cushion of a finger 6. In addition, a blood pressure sensor 105 is mounted to a blood pressure measuring portion 8.

In this embodiment, the piezoelectric devices (PZTs) are used as the piezoelectric devices 102 and 103 for measuring a blood flow velocity, and the piezoelectric device 104 for measuring a blood vessel diameter. In addition, the blood pressure measuring portion 8 is composed of a tourniquet (cuff) by which the finger 6 can be compressed at a predetermined pressure to measure a blood pressure on the basis of a pressure or the like at which the blood begins to flow. The blood pressure sensor 105 may measure the blood flow, the pulse wave and the like, and measures the pulse wave in this embodiment. Note that the finger ring portion 1 itself is composed of a tourniquet, and can also measure the blood pressure on the basis of the blood flow information measured with the circulation sensor 101.

Then, since an artery 5 residing in the finger 6 passes through both sides of the cushion of the finger 6 to extend to the tip of the finger, for the purpose of measuring the flow of the blood through the artery, the piezoelectric devices 102 and 103 for measuring a blood flow velocity, as shown in FIG. 2, are attached to the portion which is shifted to the left-hand side from the center of the cushion of the finger 6 so that an ultrasonic wave can be accurately made incident in the vicinity of the artery. Thus, the reflected ultrasonic wave from the artery can be reliably captured and hence the accuracy of measuring the blood flow is enhanced. Note that, while in the first embodiment, the piezoelectric devices 102 and 103 for measuring the blood flow velocity are attached so as to be shifted to the left-hand side, even when they are attached so as to be shifted to the right-hand side in the vicinity of the artery on the right-hand side, the same effects can be provided.

Note that, even if an ultrasonic wave is made incident to the inside of a living body, if the intensity of the ultrasonic wave is set to a low level, then the ultrasonic wave is free from harm. Also, since the ultrasonic wave is hardly influenced by a color of a skin, and disturbance light as compared with light or the like, it is suitable for a circulation dynamics measuring apparatus.

In addition, a construction for a holding method or the like of blocking disturbance light is devised, whereby it is also possible to use a sensor utilizing light or the like.

For example, the finger ring portion 1 is put on the finger 6, and the signal processing portion 2 and the blood pressure measuring portion 8 are taken with an arm to allow the circulation dynamics measuring apparatus of the first embodiment to be carried at all times. In addition, for example, the signal processing portion 2, similarly to the finger ring portion 1, may also be put on the finger 6. The signal processing portion 2, and the piezoelectric devices 102 and 103 for measuring a blood flow velocity and the piezoelectric device 104 for measuring a blood vessel diameter which are installed in the finger ring portion 1 are connected to each other through conductors. Then, a driving voltage signal, and a voltage signal measured with the piezoelectric device 103 for measuring a blood flow velocity are inputted to the piezoelectric device 102 for measuring a blood flow velocity from the signal processing portion 2 and to the signal processing portion 2 through the conductors, respectively.

FIG. 4 is a block diagram showing an internal configuration of the signal processing portion 2 of the circulation dynamics measuring apparatus of the first embodiment, and a state of connection among the signal processing portion 2, the circulation sensor portion 101 and a blood pressure sensor 105. As shown in the figure, the signal processing portion 2 is schematically constituted by driving portions 302 and 305, reception portions 301 and 303, a signal arithmetic operation portion 304 and an output portion 306.

The driving portions 302 and 305 of the first embodiment transmit driving voltages used to vibrate the piezoelectric device 102 for measuring a blood flow velocity and the piezoelectric device 104 for measuring a blood vessel diameter which are installed in the circulation sensor 101, respectively, to make an ultrasonic wave incident towards the blood vessel 5. The reception portions 303 and 301 receive the voltages which are generated when the piezoelectric device 103 for measuring a blood flow velocity and the piezoelectric device 104 for measuring a blood vessel diameter receive the ultrasonic waves, respectively.

The signal arithmetic operation portion 304 executes the processing program stored in a memory region (not shown) provided therein to execute the various processings concerned with the measurement of the circulation dynamics to thereby output the processing results to the output portion 306. In addition, the signal arithmetic operation portion 304 compares a frequency of the ultrasonic wave generated from the piezoelectric device 102 for measuring a blood flow velocity with a frequency of the ultrasonic wave received by the piezoelectric device 103 for measuring a blood flow velocity to thereby calculate the Doppler effect of the blood flow. Then, the signal arithmetic operation portion 304 calculates the flow velocity of the blood flowing through the blood vessel 5 on the basis of the change in frequency to obtain the time change in velocity.

Next, the description will hereinbelow be given with respect to a method of measuring a circulation dynamics of the first embodiment. The time changes of the blood flow velocity v, the blood vessel diameter d and the blood pressure V accompanying the pulsation of the pulse are shown in the form of graphs in FIG. 5. Here, when the blood flow rate is Q, the following Expression (2) is established:

$$Q = 1/2 \times \pi \times (d/2)^2 \times v = 1/8 \times \pi d^2 v \quad \text{(Expression 2)}.$$

Also, the resistance R of the blood vessel is expressed as follows by referring to Expression (1'):

$$R = \rho \times r = V/Q = 8V/\pi d^2 v \quad \text{(Expression 3)}.$$

Here, for the difference V in blood pressure, it is desirable to measure the difference in blood pressure between two different points in the blood vessel 5 (the left-hand and right-hand side parts between which the finger ring portion 1 is held in FIG. 3). However, since the internal pressure of a vein is so low as to be 5 to 15 mmHg, whereas the internal pressure of an artery is so high as to be about 100 mmHg, the one-side blood pressure is regarded as 0 mmHg this time and only the one-side blood pressure on the artery side will be measured.

The correlation appears between R obtained by the calculation using Expression (3) with respect to the diameter d and the blood pressure V at a time point when the blood flow in the pulses of FIG. 5 gets a maximum blood flow velocity Vmax, and the above-mentioned blood rheology, and hence it is confirmed that the correlation concerned can be utilized as the index of the circulation dynamics. For this reason, the blood flow velocity v, the blood vessel diameter d and the blood pressure V are measured to allow the state of the circulation to be accurately grasped.

For example, when the blood vessel resistance R is large, it is safely said that the blood is in the state in which the blood rheology is high and hence the viscosity of the blood is high.

Note that, while it is desirable to use the maximum blood pressure value—the minimum blood pressure value for the blood pressure V, it is confirmed that in the case or the like where the measurement is difficult to be carried out, even only the maximum blood pressure value can be utilized as a certain measure of an index.

In addition, the blood vessel resistance R is changed depending on the viscosity of the blood. However, when the blood vessel resistance R is regarded as being substantially fixed for each subject, if the blood vessel resistance R is calculated once on the basis of Expression (3), hereinafter, the blood vessel diameter d and the blood flow velocity v are measured, whereby the blood pressure V can also be roughly estimated.

Moreover, if the blood is collected once to measure the viscosity p of the blood to thereby derive the blood vessel shape resistance component r of a subject, then hereinafter the blood viscosity component p can be more accurately measured by the measurement of the blood vessel diameter d, the blood flow velocity v and the blood pressure V since it is difficult to consider that r is largely varied day by day. Further, since the value of r is the shape resistance component of the blood vessel, it can be utilized as the index as well of the degree of arteriosclerosis of the arteries or the like.

Second Embodiment

A second embodiment is an embodiment in the case where the construction of the circulation sensor 101 for use in the circulation dynamics measuring apparatus of the present invention is changed.

Figure 6:
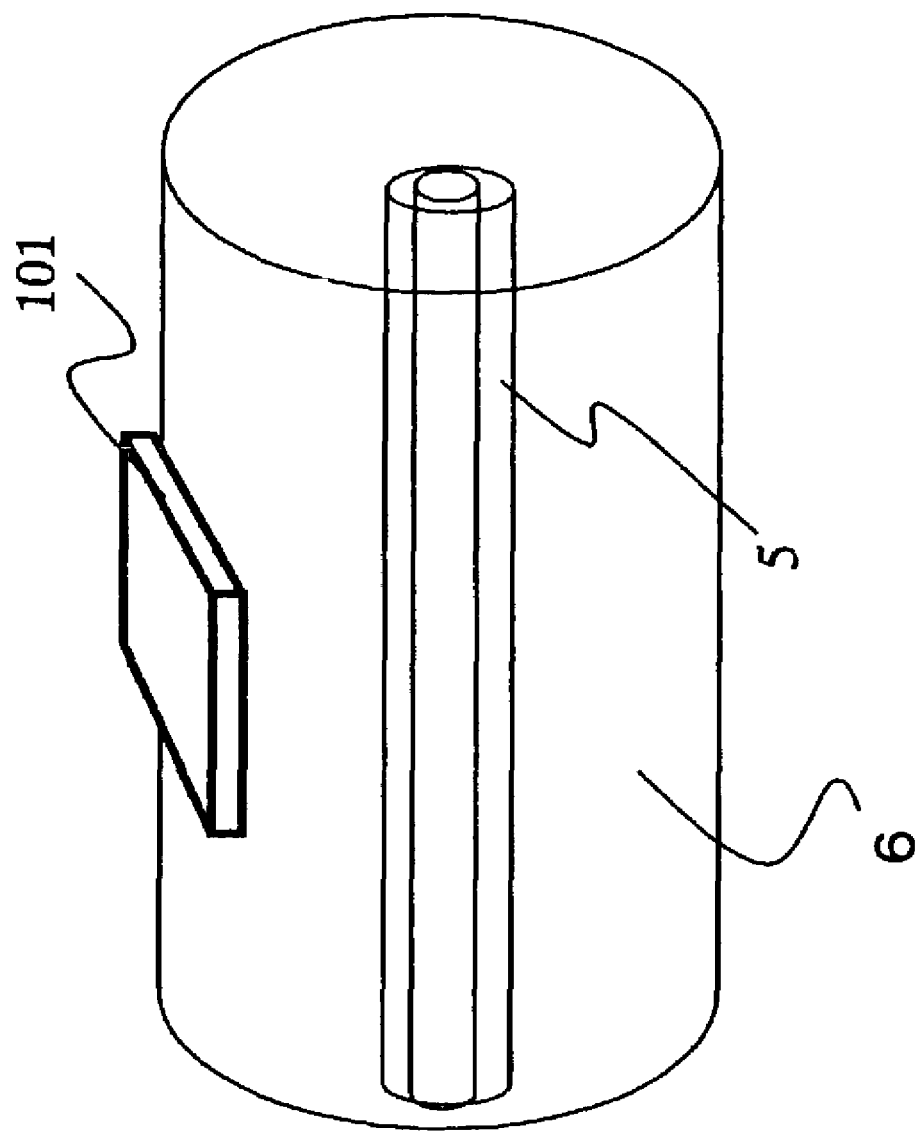
FIG. 6 is a perspective view showing a positional relationship between a circulation sensor according to a second embodiment of the present invention and a blood vessel.
Figure 7:
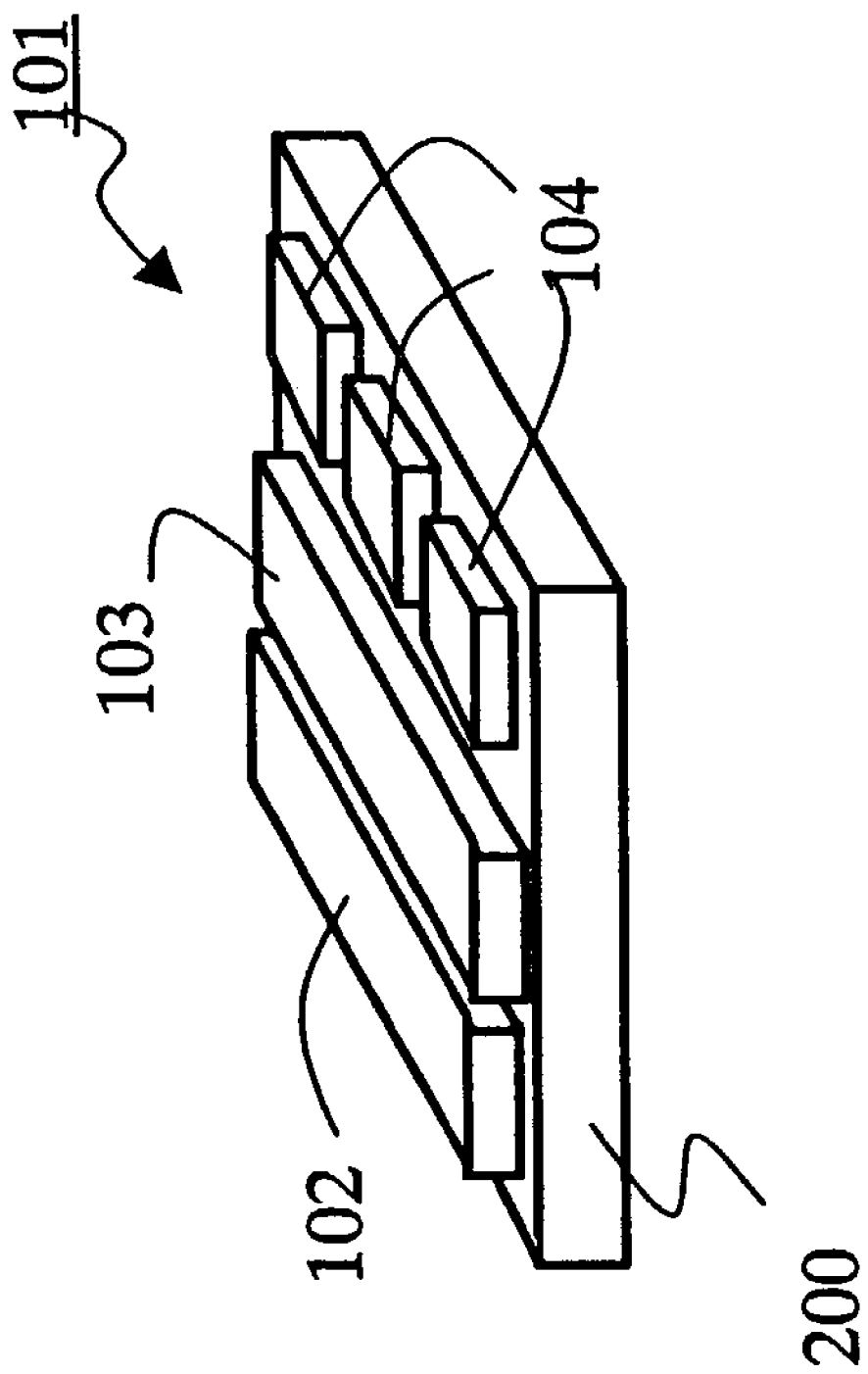
FIG. 7 is a perspective view showing a construction of the circulation sensor of the second embodiment.
Figure 8:
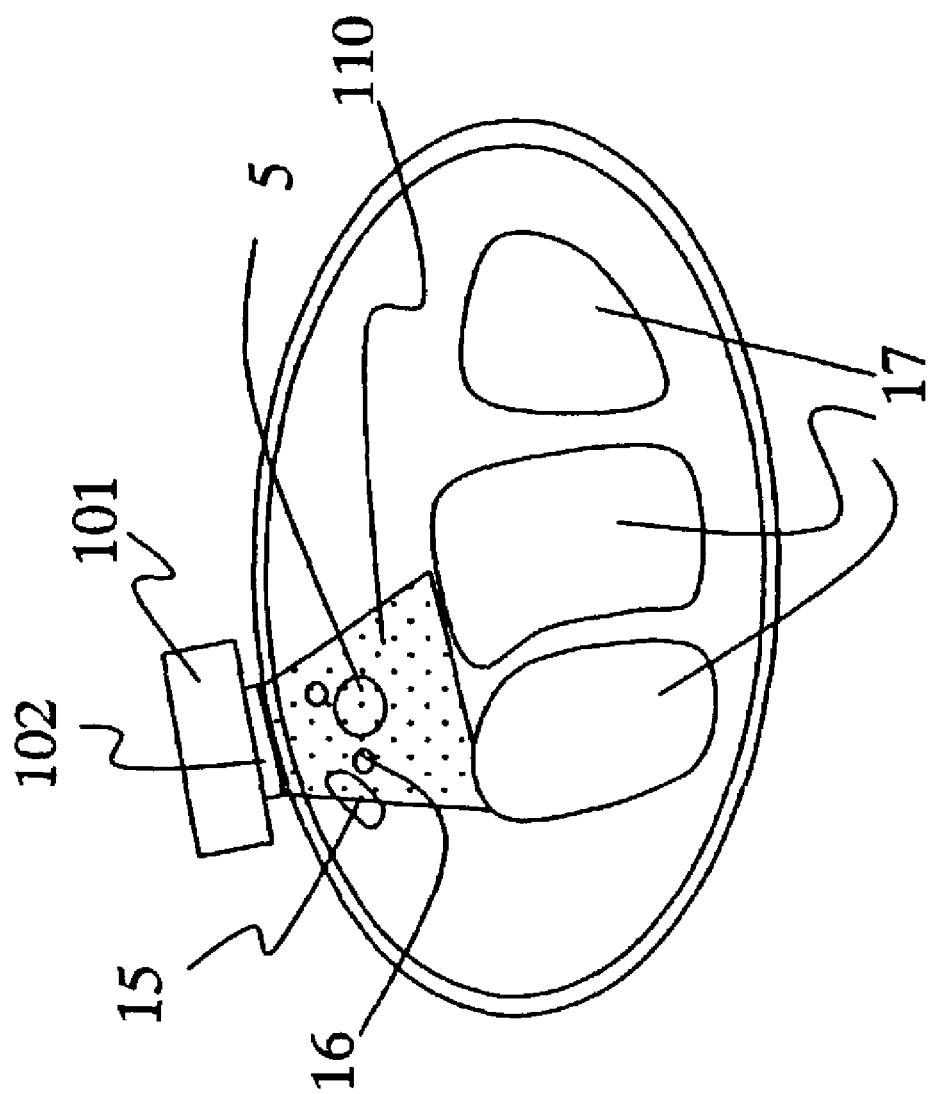
FIG. 8 is a schematic cross sectional view showing a state in which an ultrasonic wave is radiated.
Figure 9:
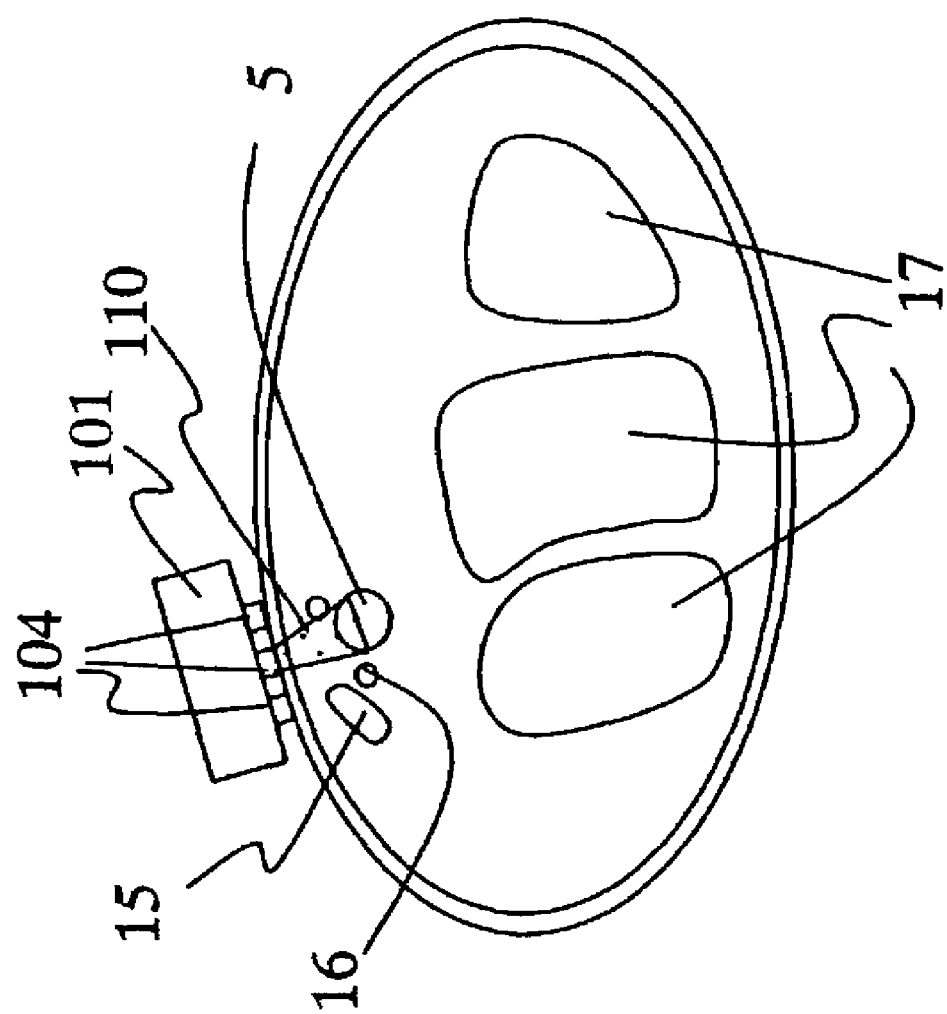
FIG. 9 is a schematic cross sectional view showing a state in which an ultrasonic wave is radiated.

FIG. 6 is a schematic view useful in explaining an arrangement of the finger 6, the blood vessel 5 and the circulation sensor 101, FIG. 7 is a perspective view showing the construction of the circulation sensor 101, and FIGS. 8 and 9 are respectively schematic cross sectional views each useful in explaining a state in which an ultrasonic wave is transmitted from the circulation sensor 101.

The circulation sensor 101, as shown in FIG. 7, is constituted by the piezoelectric devices 102 and 103 for measuring a blood flow velocity, the piezoelectric device 104 for measuring a blood vessel diameter, and a substrate 200. Note that there are not illustrated wirings through which the piezoelectric devices 102, 103 and 104 are connected to a driving circuit in order to vibrate these piezoelectric devices, electrodes provided in the piezoelectric devices, and an acoustic registration layer provided for the purpose of facilitating the effective propagation of the ultrasonic wave into the inside of a living body and of protecting the electrodes of the piezoelectric devices.

As shown in FIG. 8, an ultrasonic wave is transmitted to the inside of a living body by the piezoelectric device 102 for measuring a blood flow velocity. A beam 110 of the ultrasonic wave is reflected by a blood vessel 5, a tendon 15, a vein 16 and a bone 17 which are tissues of the inside of a living body to be received by the piezoelectric device 103 for measuring a blood flow velocity. At this time, the transmitted ultrasonic wave is reflected by the blood (red cells) flowing through the blood vessel 5. Since the red cells are moved, the frequency of the received ultrasonic wave is changed due to the Doppler effect corresponding to this movement velocity. The blood flow velocity can be measured on the basis of the Doppler shift frequency.

Since any of other tissues is not moved, in this case, even if the divergent range of the ultrasonic wave beam 110 is wide, any of other tissues does not exert a large influence on the measurement results. Conversely, since the ultrasonic wave beam 110 is more readily aligned with the blood vessel 5 as the divergent range of the ultrasonic wave beam 110 is wider, the measurement becomes easy to be carried out.

On the other hand, in the case of measurement of the blood vessel diameter, if the divergent range of the ultrasonic wave beam is wide as shown in FIG. 8, then an unnecessary reflection is caused by the bone 17, the tendon 15 and the vein 16, and hence, a bad influence is exerted on the measurement results.

For this reason, it is desirable that as shown in FIG. 9, the divergent range of the ultrasonic wave beam 110 of the piezoelectric device 104 for measuring a blood vessel diameter is made narrower so as not to be irradiated to any of the tissues other than the blood vessel 5. Note that the blood vessel diameter can be measured by measuring a time difference of the ultrasonic wave reflected by an internal wall of the blood vessel.

At this time, since the divergent range of the ultrasonic wave beam 110 is narrow, the ultrasonic wave beam 110 is difficult to be aligned with the blood vessel 5. However, as shown in FIG. 7, a plurality of sheets of piezoelectric devices 104 for measuring a blood vessel diameter are provided, and under this condition, the intensities of the reflected ultrasonic waves from the blood vessel 5 are measured. Then, the piezoelectric device 104 for measuring a blood vessel diameter is selected to be used which measures the maximum intensity of the reflected ultrasonic wave to thereby be capable of coping with this difficult alignment.

In the case of this embodiment, a PZT which is 0.5×8 mm in outside dimension, 0.2 mm in thickness, and 9.6 MHz in driving frequency is used as each of the piezoelectric devices 102 and 103 for measuring a blood flow velocity, and a PZT which is 2×2 mm in outside dimension, 0.2 mm in thickness, and 9.6 MHz in driving frequency is used as the piezoelectric device 104 for measuring a blood vessel diameter.

Note that, with respect to the driving frequency as well, the frequency suitable for the piezoelectric devices 102 and 103 for measuring a blood flow velocity is different from that suitable for the piezoelectric device 104 for measuring a blood vessel diameter.

When an acoustic velocity in a living body is c, an ultrasonic wave incident angle is θ, and a driving frequency is f, the Doppler shift frequency change Δf due to the blood flow velocity v is expressed by the following Expression (4):

$$\Delta f = 2vf \times \cos\theta/c \quad \text{(Expression 4)}.$$

Hence, Δf is further increased as the driving frequency f is higher, which has the superior advantage in the later signal processing and the like. However, a relationship between the driving frequency f and an attenuation coefficient of an ultrasonic wave inside a living body is expressed as follows:

$$H = H0e - 2\alpha lf \quad \text{(Expression 5)}.$$

where l is a distance to the blood vessel, α is an attenuation factor, and H0 is an amplitude at a distance of 0. Hence, since the intensity of the ultrasonic wave is further reduced as the frequency f is higher, the higher frequency is not necessarily preferable.

Moreover, when the blood also flows through the vein 16 as well, its velocity is taken into consideration (it is desirable to be able to separate this velocity), the velocity of the blood flowing through the vein 16 is slower than that of the blood flowing through the artery. Thus, if the difference of the Doppler shift frequency due to the difference in blood flow velocity is made large, the velocity of the blood flowing through the vein 16 can be separated from that of the blood flowing through the artery. In order to attain this, it is necessary to increase the driving frequency.

Taking the foregoing into consideration, it is most preferable that the driving frequency of the piezoelectric devices 102 and 103 for measuring a blood flow velocity is in the range of about 5 to 10 MHz.

On the other hand, in the case of the piezoelectric device 104 for measuring a blood vessel diameter, a wavelength of the ultrasonic wave becomes a resolving power in a distance direction. When for example, a driving frequency is 10 MHz, and an acoustic velocity of a living body is 1,500 m/s, a wavelength is 150 μm. This wavelength becomes the resolving power.

Assuming that a blood vessel diameter of an artery of the tip of a finger is about 1 mm and its change is about 200 μm, if consideration is made together with the fact that it is more desirable that the attenuation of the ultrasonic wave is less, then the optimal driving frequency is about 7.5 MHz.

Note that, since a blood vessel diameter and a blood flow velocity of an artery differ depending on a part to be measured (a radius artery, the carotid artery or a capillary artery), the above-mentioned driving frequency will differ.

In addition, while in this embodiment, the piezoelectric devices 102 and 103 for measuring a blood flow velocity are divided into one for transmission of an ultrasonic wave and one for reception of an ultrasonic wave to be used, they may also be formed into one sheet.

Moreover, in the circulation sensor 101 as shown in FIG. 7, if the piezoelectric device 102 for measuring a blood flow velocity is used as one for transmission, when the timing at which the piezoelectric device 102 for measuring a blood flow velocity is driven is identical to the timing at which the piezoelectric devices 104 for measuring a blood vessel diameter are driven, the ultrasonic waves are propagated through the substrate 200 to exert influences on each other. This becomes a cause of a noise. For this reason, the driving timings need to be shifted from each other. In this embodiment, since the acoustic velocity of the ultrasonic wave propagated through the substrate 200 is 2,500 m/s, and the distance between the piezoelectric device 102 for measuring a blood flow velocity and the piezoelectric devices 104 for measuring a blood vessel diameter is set to 5 mm, a period of time required for the ultrasonic wave transmitted from the piezoelectric device 102 for measuring a blood flow velocity to be propagated up to the piezoelectric devices 104 for measuring a blood vessel diameter becomes 2 s. Thus, the driving timings need to be shifted by equal to or larger than that time difference.

Note that, with respect to the ultrasonic waves reflected by the blood vessel 5, the piezoelectric device 102 for measuring a blood flow velocity and the piezoelectric devices 104 for measuring a blood vessel diameter are separated in distance by about 5 mm. Thus, the reflection areas do not overlap with each other, and hence, there is no need to take the inter-reflection of the reflected waves into consideration. However, when both the piezoelectric devices are disposed close to each other, and so forth, there is need to take this influence as well into consideration.

Third Embodiment

A third embodiment is an embodiment in the case where the construction of the circulation sensor for use in the circulation dynamics measuring apparatus of the present invention is changed.

Figure 10:
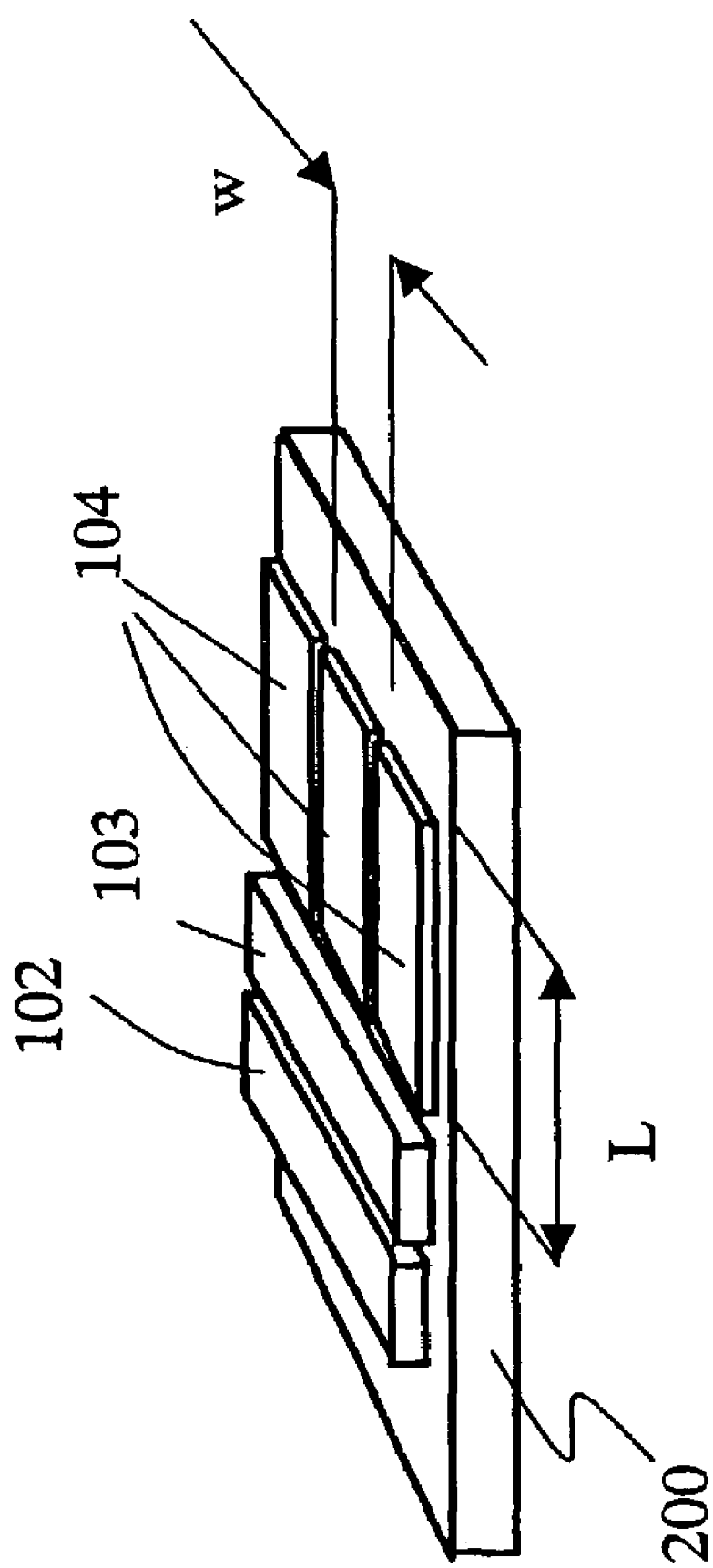
FIG. 10 is a perspective view showing a construction of a circulation sensor according to a third embodiment of the present invention.
Figure 11:
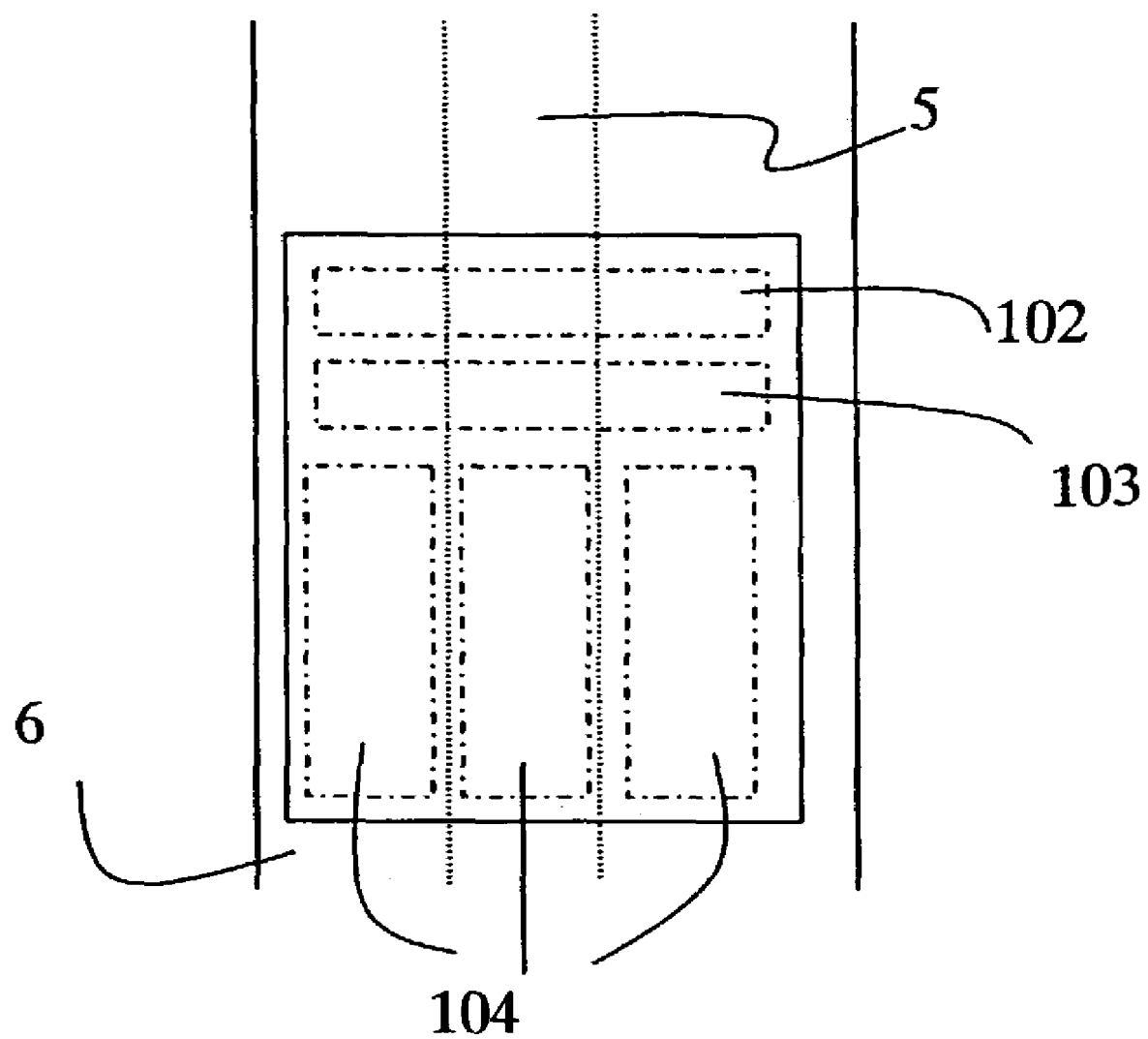
FIG. 11 is a view showing the positional relationship between the circulation sensor according to the third embodiment of the present invention and the blood vessel.

An example of the circulation sensor 101 is shown in FIG. 10. FIG. 11 is a schematic view useful in explaining a positional relationship between the circulation sensor 101 and a blood vessel. Incidentally, a blood pressure measuring portion and a processing portion are not illustrated in the figures.

In general, since an ultrasonic wave from a PZT becomes close to a spherical wave as an area of the PZT is smaller, the divergent angle of the ultrasonic wave beam becomes wide (directivity becomes low).

For this reason, if the area is made too small, the reflection from the tissues of a living body other than the blood vessels becomes large to remarkably reduce the measurement accuracy. In addition, if the divergent angle of the ultrasonic wave beams becomes wide, then the intensity of the ultrasonic wave which is reflected to be received by the same piezoelectric device is also reduced. Thus, with respect to the piezoelectric device, it is desirable that its area is increased as much as possible and also its shape is such that the ultrasonic wave is hardly irradiated by any of the tissues other than the blood vessels.

Furthermore, if both a width W and a length L of a piezoelectric device shown in FIG. 10 are made small, then a vibration mode in a longitudinal direction of the piezoelectric device becomes close to the vibration mode in a thickness direction thereof, and hence the piezoelectric device can not be effectively vibrated at a desired frequency in a thickness direction. For this reason, a certain measure of a length is required for each of the length and the width of the piezoelectric device.

FIG. 10 shows the circulation sensor 101 in which the shape of each of the piezoelectric devices 104 for measuring a blood vessel diameter is made a rectangle, and the piezoelectric devices 104 for measuring a blood vessel diameter are arranged so as to intersect perpendicularly the longitudinal direction of the piezoelectric devices 102 and 103 for measuring a blood flow velocity.

The width W of the piezoelectric device is made slightly smaller than a blood vessel diameter, whereby the ultrasonic wave radiation area can be made substantially equal to the width of the blood vessel to allow the measurement sensitivity to be enhanced. In this embodiment, since a blood vessel of the tip of a finger is made to be an object, the width W of the piezoelectric device 104 is set to be about 0.8 mm.

In addition, if the width L of the piezoelectric device is about 6.0 mm, then the ultrasonic wave does not spread too much, and hence a blood vessel can be effectively radiated with the ultrasonic wave.

Note that a lens for converging an ultrasonic wave may also be provided on the piezoelectric device 104 for measuring a blood vessel diameter. In this case, the restriction condition is relaxed to some extent as compared with the shape as in the above-mentioned piezoelectric device.

Fourth Embodiment

A fourth embodiment is an embodiment in which the construction of the circulation sensor 101 for use in the circulation dynamics measuring apparatus of the present invention is changed.

Figure 12:
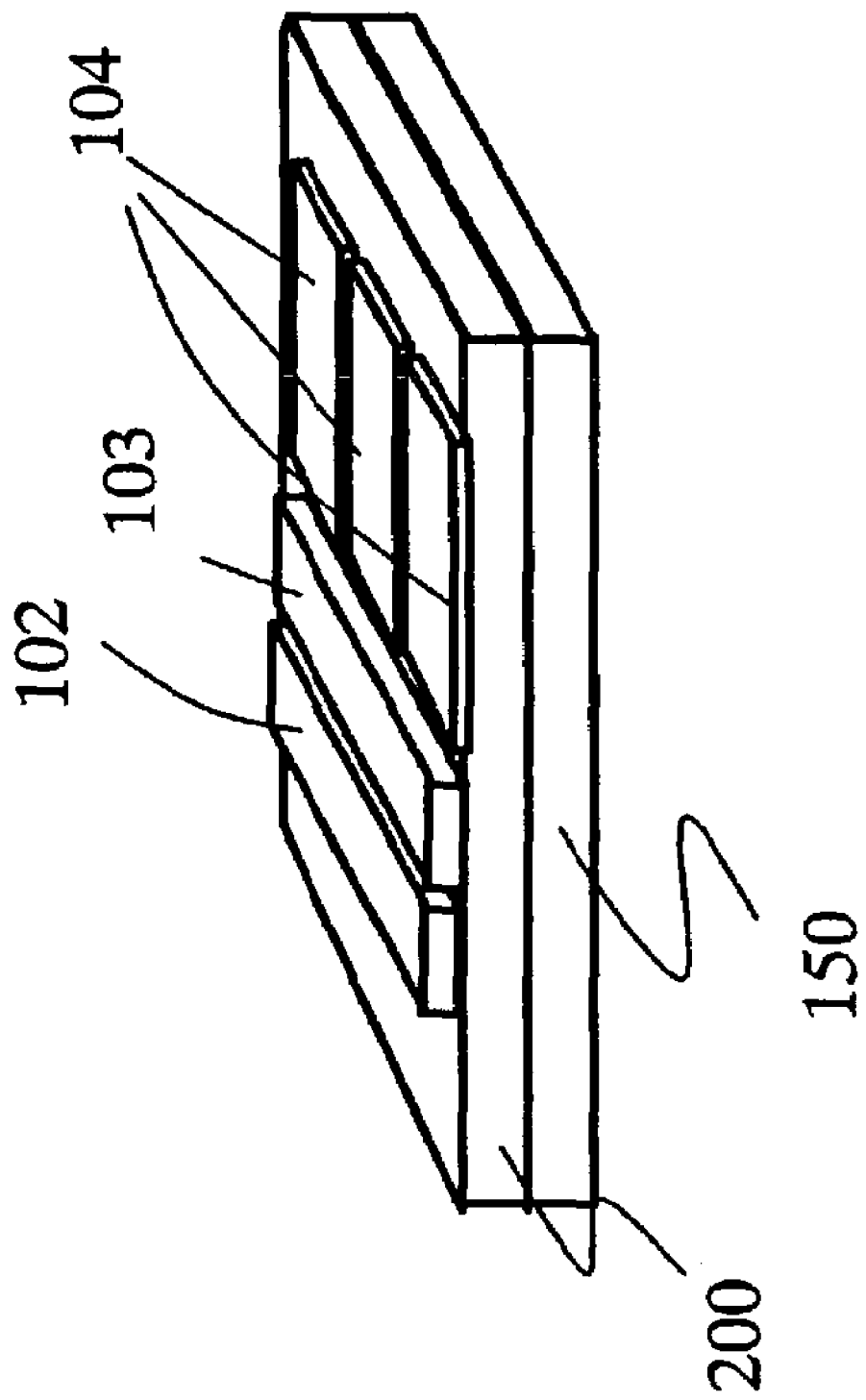
FIG. 12 is a perspective view showing a construction of a circulation sensor according to a fourth embodiment of the present invention.
Figure 13:
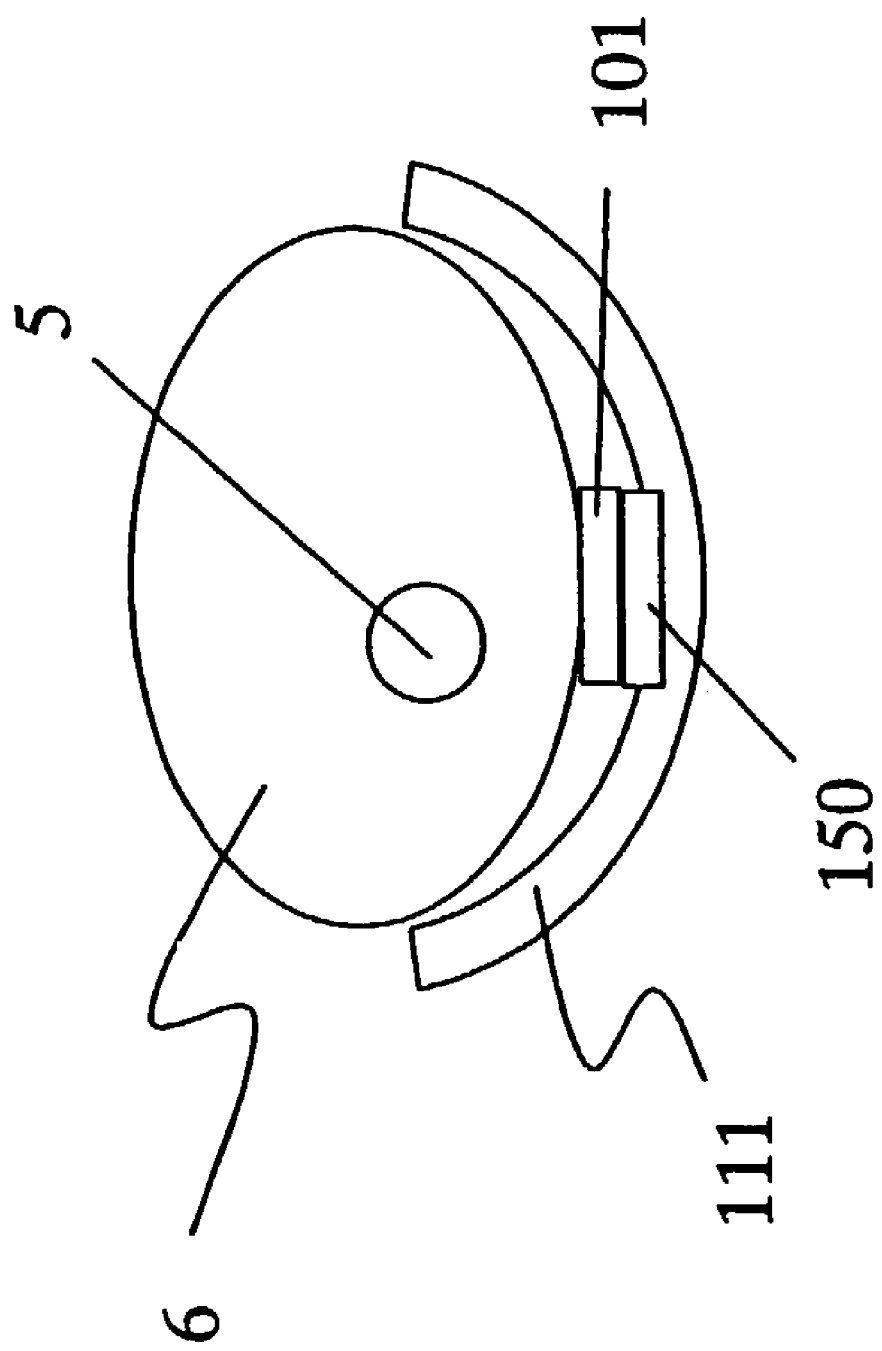
FIG. 13 is a schematic cross sectional view useful in explaining a relationship among a holding portion, a circulation sensor and a finger.

FIG. 12 is a perspective view showing one example of the circulation sensor 101, and FIG. 13 is a schematic cross sectional view useful in explaining a state in which the circulation sensor 101 is held at the tip of the finger 6. A blood pressure measuring portion and a processing portion are not illustrated in the figures.

The circulation sensor 101 shown in FIG. 12 has a construction in which there are provided the piezoelectric devices 102 and 103 for measuring a blood flow velocity, the piezoelectric devices 104 for measuring a blood vessel diameter, the substrate 200, and a piezoelectric device 150 for measuring a pressure pulse wave provided on a back surface of the substrate 200.

As shown in FIG. 13, the circulation sensor 101 is supported by a supporting portion 111, whereby the pressure fluctuation due to the contraction of a blood vessel can be measured in the form of a pressure pulse wave by the piezoelectric device 150 for measuring a pressure pulse wave. With this construction, when a blood pressure is measured once by the blood pressure measuring portion (not shown), the fluctuation in blood pressure can be roughly estimated on the basis of the measurement of the pressure pulse wave hereinafter. Thus, there is need to compress a finger with a cuff every measurement to allow the circulation sensor to be made to be easily used.

Fifth Embodiment

A fifth embodiment is an embodiment in which the construction of the circulation sensor for use in the circulation dynamics measuring apparatus of the present invention is changed.

Figure 14:
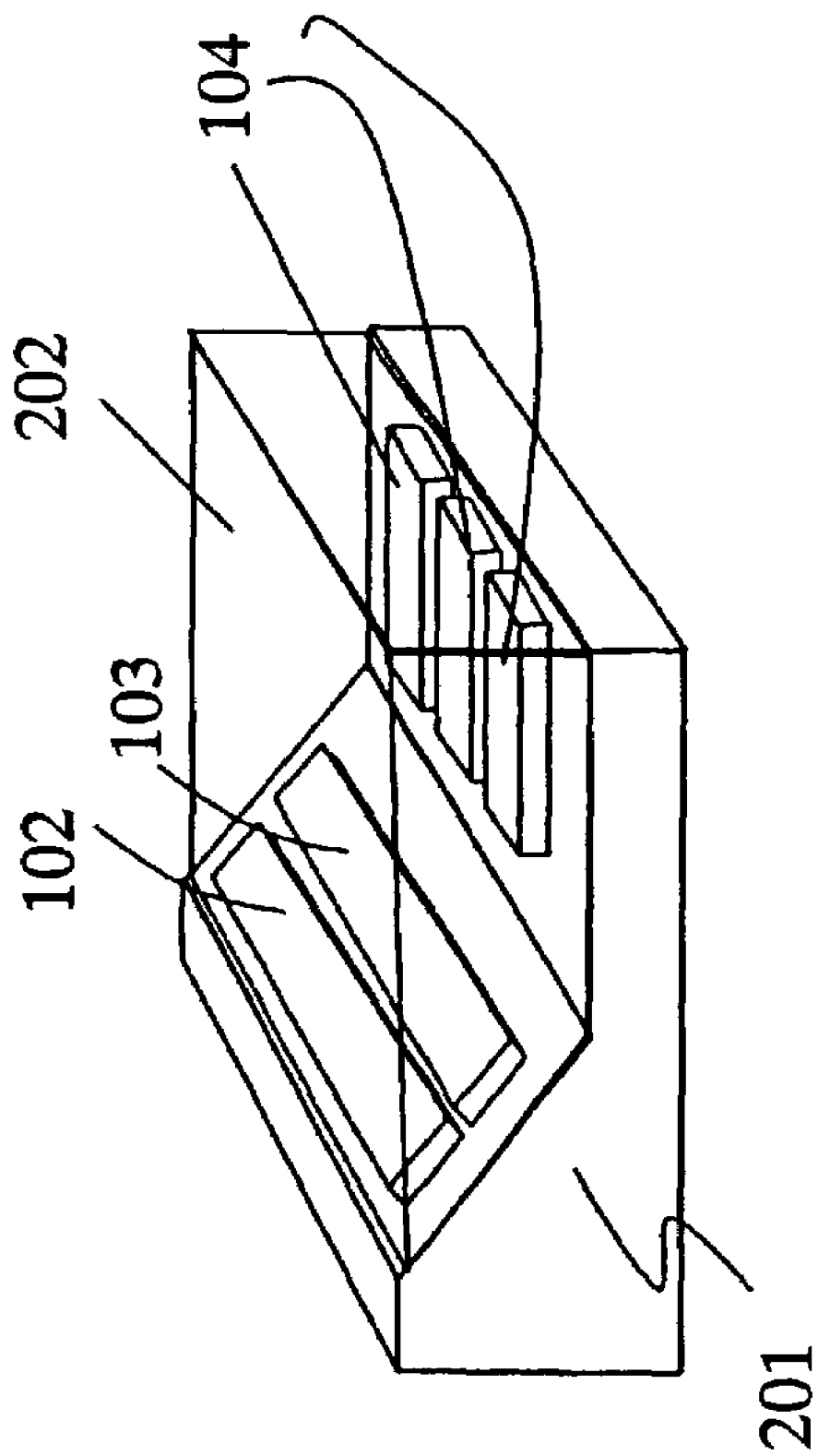
FIG. 14 is a perspective view showing a construction of a circulation sensor according to a fifth embodiment of the present invention.
Figure 15:
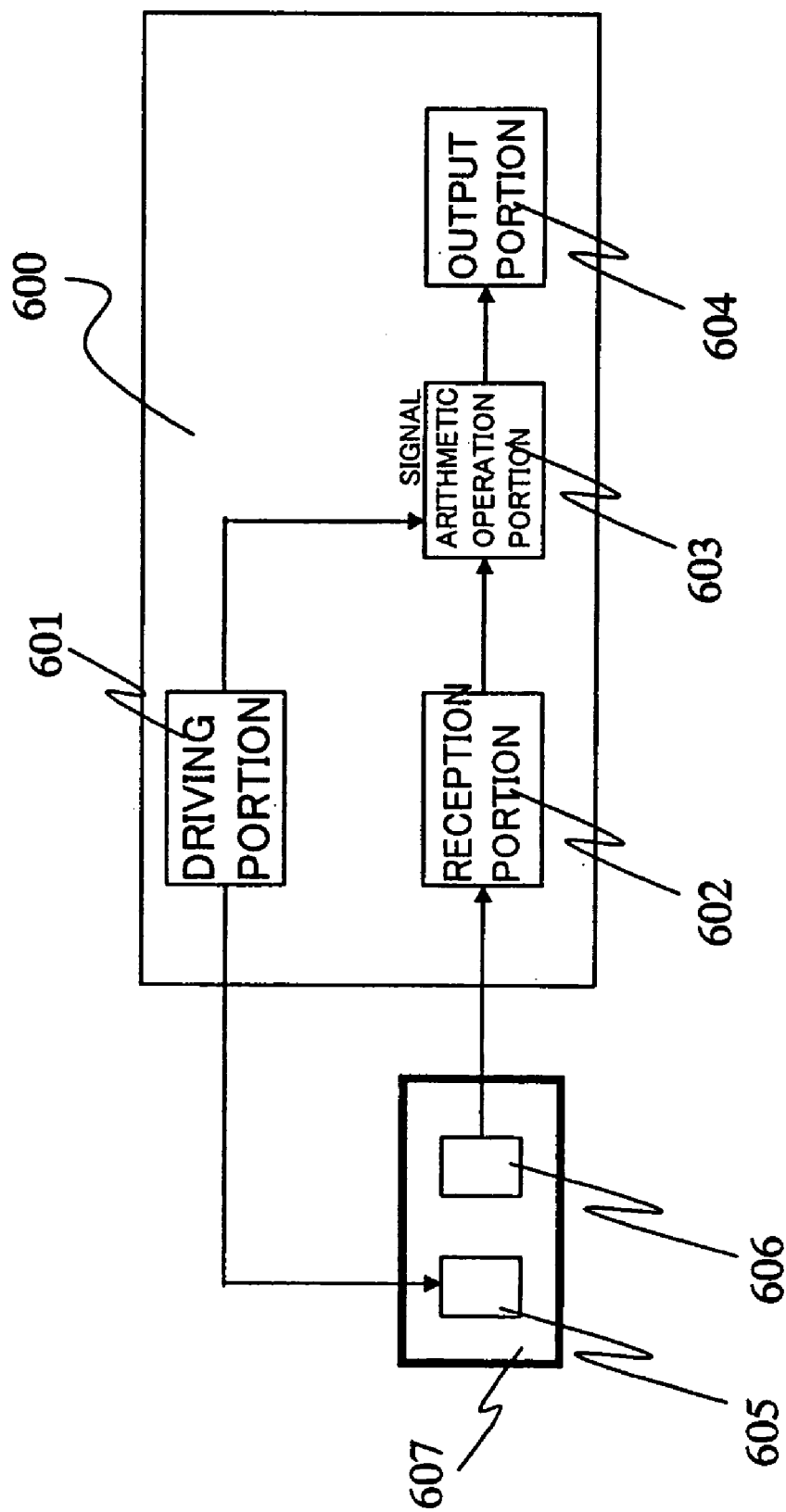
FIG. 15 is a block diagram showing a configuration of a driving circuit of a conventional circulation dynamics measuring apparatus.
Figure 16:
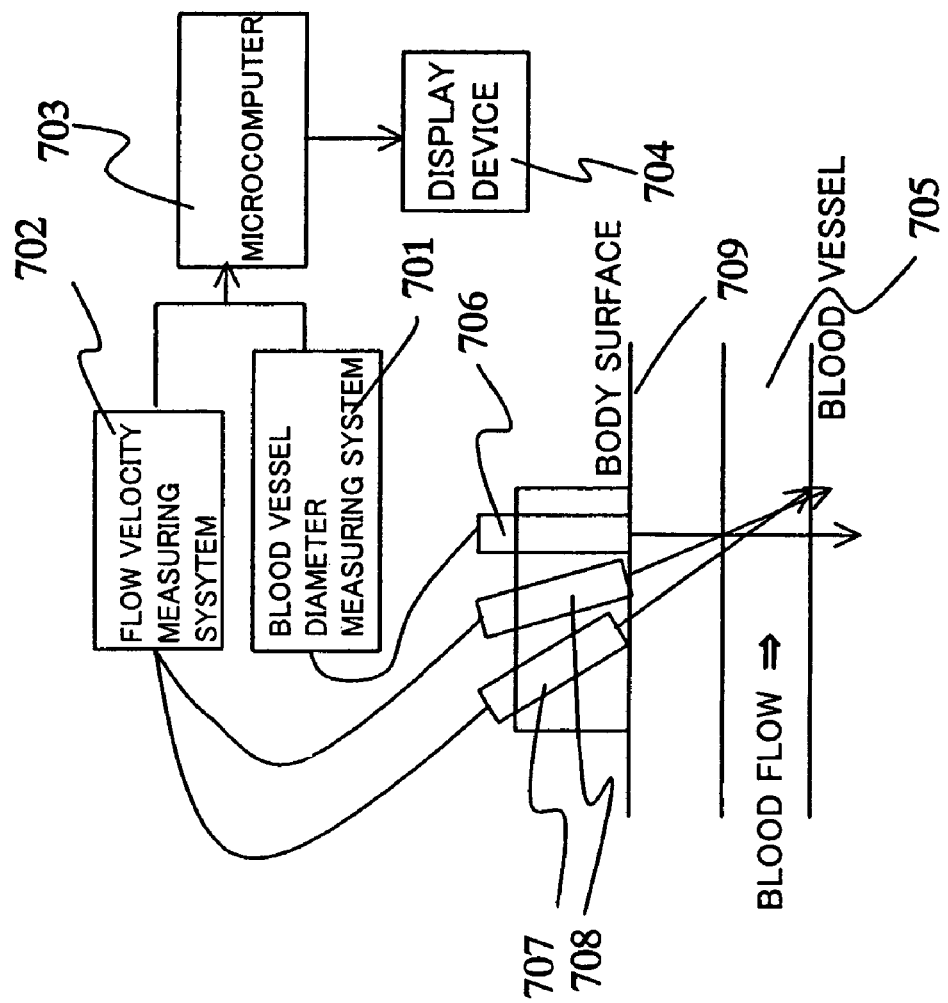
FIG. 16 is a block diagram, partly in schematic view, showing a configuration of a conventional blood flow rate measuring apparatus.

FIG. 14 is a perspective view showing one example of the circulation sensor 101.

For the piezoelectric devices 102 and 103 for measuring a blood flow velocity, as expressed in Expression (4), the frequency change due to the Doppler effect becomes larger as the ultrasonic wave incident angle θ with a blood vessel is smaller. For this reason, as shown in FIG. 14, the piezoelectric devices 102 and 103 for measuring a blood flow velocity are provided on a slant face of a substrate 201 which is formed so as to make a predetermined angle (π/2−θ) with a flat surface portion of the substrate 201. On the other hand, if the ultrasonic wave from the piezoelectric device 104 for measuring a blood vessel diameter is not made incident perpendicularly to a blood vessel, then the blood vessel diameter can not be accurately measured. For this reason, as shown in FIG. 14, the piezoelectric devices 104 for measuring a blood vessel diameter are provided on the flat surface portion of the substrate 201. Moreover, if there is irregularity on the sensor surface, then a gap will be defined between the sensor surface and a skin of a subject, and hence, there is a fear that the ultrasonic wave may be greatly attenuated through the gap. Therefore, an acoustic registration layer 202 is formed on the sensor surface to remove the irregularity to allow the state of connection between the sensor surface and a skin of a subject to be satisfactorily held.

In addition, it is also possible that an ultrasonic wave is transmitted and received by one sheet of piezoelectric device; and two stages of slant faces of the substrate 201 are provided and two sheets of piezoelectric devices are arranged on the two stages of slant surfaces, respectively, so that an absolute flow velocity can be measured on the basis of a difference in Doppler shift frequency therebetween.

As set forth hereinabove, according to the circulation dynamics measuring apparatus of the present invention, the circulation dynamics can be measured without requiring the collection of the blood. In addition, since the blood flow rate and the blood pressure can be simultaneously measured, or both the circulation information can be measured, it is possible to enhance the accuracy of the circulation dynamics to be measured.

Moreover, according to the circulation sensor of the present invention, since it is possible to provide a small and highly accurate sensor which is capable of simultaneously measuring the blood vessel diameter and the blood flow velocity, it is possible to measure the information which is important for the evaluation of the circulation dynamics such as a distal end circulation.

While the present invention has been particularly shown and described with reference to the preferred embodiments and the specified changes thereof, it will be understood that other changes and the various modifications will occur to those skilled in the art without departing from the scope and true spirit of the invention. The scope of the invention is, therefore, to be determined solely by the appended claims.

What is claimed is:

1. A method of calculating circulation dynamics of a living body, comprising:

deriving a resistance component corresponding to a shape of a blood vessel in the living body using previously obtained values of viscosity, pressure and flow rate of blood flowing in the blood vessel; and calculating information corresponding to the viscosity of the blood using the derived resistance component.

2. A method of calculating circulation dynamics of a living body, comprising:

transmitting a beam of wave energy into the living body through a surface of the living body;

receiving a reflected beam of energy reflected by a blood vessel in the living body;

measuring a diameter of the blood vessel and a flow velocity and a pressure of blood flowing in the blood vessel in accordance with the received reflected beam of energy; and calculating circulation dynamics of the living body including information corresponding to a viscosity of the blood using the measured diameter of the blood vessel the measured flow velocity, and the measured pressure of the blood.

3. A method according to claim 2; wherein the circulation dynamics is calculated utilizing a maximum value of the blood pressure.

4. A method according to claim 2; wherein the circulation dynamics is calculated utilizing a maximum value of the diameter of the blood vessel and a maximum value of the blood flow velocity.

5. A method according to claim 2; wherein the calculated circulation dynamics includes information corresponding to blood rheology.

6. A method of calculating circulation dynamics of a living body, comprising the steps of:

transmitting a beam of wave energy into a living body through a surface of the living body;

receiving a reflected beam of energy reflected by a blood vessel in the living body;

measuring a flow velocity of blood flowing in the blood vessel and a pressure of the blood in accordance with the received reflected beam of energy; and calculating circulation dynamics of the living body including a resistance component corresponding to a shape of the blood vessel using a viscosity of the blood and the measured blood pressure and blood flow velocity.

* * * * *